US007662365B2

(12) United States Patent
Bentley et al.

(10) Patent No.: US 7,662,365 B2
(45) Date of Patent: Feb. 16, 2010

(54) POLYMER CONJUGATES OF OPIOID ANTAGONISTS

(75) Inventors: Michael David Bentley, Huntsville, AL (US); Michael James Roberts, Williamsburg, VA (US); Xiaoming Shen, Madison, AL (US); Lin Cheng, Huntsville, AL (US)

(73) Assignee: Nektar Therapeutics, San Carlos, CA (US)

( * ) Notice: Subject to any disclaimer, the term of this patent is extended or adjusted under 35 U.S.C. 154(b) by 0 days.

(21) Appl. No.: 11/332,964

(22) Filed: Jan. 17, 2006

(65) Prior Publication Data

US 2006/0105046 A1    May 18, 2006

Related U.S. Application Data

(63) Continuation of application No. 10/274,296, filed on Oct. 18, 2002, now Pat. No. 7,056,500.

(60) Provisional application No. 60/330,400, filed on Oct. 18, 2001.

(51) Int. Cl.
    *A81K 31/74*    (2006.01)
(52) U.S. Cl. ............... 424/78.18; 424/78.26; 424/78.27
(58) Field of Classification Search ........................ None
    See application file for complete search history.

(56) References Cited

U.S. PATENT DOCUMENTS

| 4,366,159 | A | 12/1982 | Magruder et al. |
| 4,670,417 | A | 6/1987 | Iwasaki et al. |
| 4,719,215 | A | 1/1988 | Goldberg |
| 4,730,048 | A | 3/1988 | Portoghese |
| 4,806,556 | A | 2/1989 | Portoghese |
| 4,861,781 | A | 8/1989 | Goldberg |
| 5,053,228 | A | 10/1991 | Mori et al. |
| 5,102,887 | A | 4/1992 | Goldberg |
| 5,159,081 | A | 10/1992 | Cantrell et al. |
| 5,225,206 | A | 7/1993 | Fushimi et al. |
| 5,250,542 | A | 10/1993 | Cantrell et al. |
| 5,270,328 | A | 12/1993 | Cantrell et al. |
| 5,434,171 | A | 7/1995 | Frank et al. |
| 5,567,422 | A | 10/1996 | Greenwald |
| 5,618,926 | A | 4/1997 | Salamone et al. |
| 5,866,164 | A | 2/1999 | Kuczynski et al. |
| 5,972,954 | A | 10/1999 | Foss et al. |
| 6,362,254 | B2 | 3/2002 | Harris et al. |
| 6,419,959 | B1 | 7/2002 | Walter et al. |
| 6,451,806 | B2 | 9/2002 | Farrar |
| 6,515,100 | B2 | 2/2003 | Harris |
| 6,703,381 | B1 | 3/2004 | Ekwuribe et al. |
| 2002/0182172 | A1 | 12/2002 | Bentley et al. |
| 2003/0044402 | A1 | 3/2003 | Nelson |
| 2003/0105275 | A1 | 6/2003 | Bentley et al. |
| 2004/0023852 | A1 | 2/2004 | Roberts et al. |
| 2005/0136031 | A1 | 6/2005 | Bentley et al. |
| 2006/0182692 | A1 | 8/2006 | Fishburn et al. |
| 2009/0221766 | A1 | 9/2009 | Cheng et al. |

FOREIGN PATENT DOCUMENTS

| EP | 0995757 | 4/2000 |
| WO | WO 93/24476 A1 | 12/1993 |
| WO | WO 96/21469 A1 | 7/1996 |
| WO | WO 99/45964 A1 | 9/1999 |
| WO | WO 01/19407 | 3/2001 |
| WO | WO 01/47562 | 7/2001 |
| WO | WO 01/62299 | 8/2001 |
| WO | WO 02/065988 | 8/2002 |
| WO | WO 02/089789 | 11/2002 |
| WO | WO 03/032990 | 4/2003 |
| WO | WO 03/037384 | 5/2003 |
| WO | WO 03/037385 | 5/2003 |
| WO | WO 03/051113 A1 | 6/2003 |
| WO | WO 03/079972 A2 | 10/2003 |
| WO | WO 03/101476 A1 | 12/2003 |
| WO | WO 2004/082620 | 9/2004 |

OTHER PUBLICATIONS

Chemicalland21 disclosure "2'-Deoxycytidine" Downloaded from the world wide web on Dec. 22, 2006.*
Penn, N.W. "Deoxycytidine: a morphine antagonist" Arch Intl Pharmacodyn Ther May 1978;233(1):145-55.*
Asai et al., "Naloxone Inhibits Gastric Emptying in the Rat", *Anesth. Analg.*, 1999, pp. 204-208, vol. 88.
Batz et al., "Pharmacologicaly Active Polymers 9th Report: Retard Forms of Morphine Antagonists", *Arzneimittel-Forshung*, 1997, pp. 1884-1888, vol. 27 (ii), No. 10.
Bennett et al., "Biodegradable Polymeric Prodrugs of Naltrexone", *Journal of Controlled Release*, 1991, pp. 43-52, vol. 16, Nos. 1/2.
Bennett et al., "Drug-Coupled Poly(Amino Acids) as Polymeric Prodrugs", *Journal of Bioactive and Compatible Polymers*, 1988, pp. 44-52, vol. 3.
Fishman, J., et al., "Preparation and Evaluation of a Sustained Naloxone Delivery System in Rats," *Pharmacology*, 1975, pp. 513-519, vol. 13(6).
Greenwald, R., et al., "Highly Water Soluble Taxol Derivatives: 7-Polyethylene Glycol Carbamates and Carbonates," *J. Org. Chem.*, 1995, pp. 331-336, vol. 60.
Harris, J. M., ed., "Poly(Ethylene Glycol) Chemistry—Biotechnical and Biomedical Applications," 1992, pp. 1-10, Plenum Press, New York.

(Continued)

*Primary Examiner*—Eric E. Silverman
(74) *Attorney, Agent, or Firm*—Jones Day

(57) ABSTRACT

The invention provides polymer conjugates of opioid antagonists comprising a polymer, such as poly(ethylene glycol), covalently attached to an opioid antagonist. The linkage between the polymer and the opioid antagonist is preferably hydrolytically stable. The invention also includes a method of treating one or more side effects associated with the use of opioid analgesics, such as constipation, nausea, or pruritus, by administering a polymer conjugate of the invention.

22 Claims, No Drawings

OTHER PUBLICATIONS

Jiang et al., "Stereochemical Studies on Medicinal Agents. 23.[1] Synthesis and Biological Evaluation of 6-Amino Derivatives of Naloxone and Naltrexone", *J. Medicinal Chemistry*, 1977, pp. 1100-1103, vol. 20, No. 8.

Johansson et al., "Effect of some poly(ethylene glycol)-bound and dextran-bound affinity ligands on the partition of synaptic membranes in aqueous two-phase systems", *J. Chromatogr. B*, 1994, pp. 137-147, vol. 652.

Lapicque et al., "Polysaccharidic Prodrugs for Enzymatically Controlled Release", *Journal of Controlled Release*, 1986, pp. 39-45, vol. 4.

Li et al., "Poly($\alpha$-Amino Acid)-Drug Conjugates—A Biodegradable Injectable Drug Delivery System", *Polymer Preprints (American Chemical Society, Division of Polymer Chemistry)*. 1990, pp. 198-199, vol. 21, No. 2.

Mahkam et al., "Preparation of new biodegradable polyurethanes as a therapeutic agent", *Polymer Degradation and Stability*, 2003, pp. 199-202, vol. 80.

Negishi et al., "Coupling of Naltrexone to Biodegradable Poly($\alpha$-Amino Acids)", *Pharmaceutical Research*, 1987, pp. 305-310, vol. 4, No. 4.

Olde et al., "Affinity Partitioning and Centrifugal Counter-Current Distribution of Membrane-Bound Opiate Receptors Using Naloxone-Poly(Ethylene Glycol)"., *Neuroscience*, 1985, pp. 1247-1253, vol. 15, No. 4.

Pasternak et al., "Macromolecular Naloxone: A Novel Long-Acting Polymer-Bound Drug", *Life Sciences*, 1976, pp. 977-982, vol. 18.

Sidman et al., "Use of Synthetic Polypeptides in the Preparation of Biodegradable Delivery Systems for Narcotic Antagonists", *Synthetic Polypeptide Systems*, 1980, pp. 214-231.

Takahashi, R.N., et al., "Effects of Ketamine on Nociception and Gastrointestinal Motility in Mice Are Unaffected by Naloxone," *pGen. Pharmac.*, 1987, pp. 201-203, vol. 18(2), Pergamon Journals Ltd.

Yolles, S., et al., "Long Acting Delivery Systems for Narcotic Antagonists II: Release Rates of Naltrexone from Poly(lactic Acid) Composites," *Journal of Pharmaceutical Sciences*, Feb. 1975, pp. 348-349, vol. 64(2).

Zalipsky, Samuel., "Chemistry of Polyethylene Glycol Conjugates with Biologically Active Molecules", *Advanced Drug Delivery Reviews*, 1995, pp. 157-182, vol. 16.

Zalipsky, S., "Functionalized Poly(ethylene glycol) for Preparation of Biologically Relevant Conjugates," *Bioconjugate Chem.*, 1995, pp. 150-165, vol. 6, American Chemical Society, USA.

Erez et al., "Narcotic Antagonistic Potency of Bivalent Ligands Which Contain $\beta$-Naltrexamine. Evidence for Bridging between Proximal Recognition Sites", *J. Med. Chem.*, 1982, pp. 847-849, vol. 25, No. 7.

Eldon, et al., "NKTR-118 (Oral PEG-Naloxol), a PEGylated Dervative of Naloxone: Demonstrations of Selective Peripheral Opioid Antagonism After Oral Administration in Preclinical Models," Poster 28 presented at the American Academy of Pain Management 18th Annual Clinical Meeting; Sep. 27-30, 2007; Las Vegas, NV.

ISA, International Search Report dated Mar. 28, 2003 for PCT/US02/33325.

ISA, International Search Report and Written Opinion dated Nov. 28, 2005 for PCT/US04/042661.

The Merck Index, 12th Edition (Merck & Co., Inc. Whitehouse Station N.J., 1996), entry 6449, pp. 1092-1093.

Nektar Therapeutics, "Nektar Announces Positive Results from Phase 2 Study of Oral NKTR-118 in Patients with Opioid-Induced Constipation (OIC)," PRNewswire dated Mar. 2, 2009.

Neumann et al., "Clinical Investigation of NKTR-118 as a Selective Oral Peripheral Opioid Antagonist," Poster 27 Presented at the American Academy of Pain Management 18th Annual Clinical Meeting; Sep. 27-30, 2007; Las Vegas, NV.

Yamashita et al., "Micelle Monomer Control over the Membrane-Disrupting Properties of an Amphiphilic Antibiotic", J. Am. Chem. Soc., 1995; pp. 6249-6253, vol. 117.

* cited by examiner

POLYMER CONJUGATES OF OPIOID ANTAGONISTS

CROSS-REFERENCE TO RELATED APPLICATIONS

This application is a continuation of U.S. application Ser. No. 10/274,296, filed Oct. 18, 2002 now U.S. Pat. No. 7,056,500, which claims the benefit of Provisional Application Ser. No. 60/330,400, filed Oct. 18, 2001, all of which are incorporated herein by reference in their entirety.

FIELD OF THE INVENTION

This invention relates to water-soluble polymer conjugates of biologically active molecules, and in particular, to water-soluble polymer conjugates of opioid antagonists, such as naloxone, and related pharmaceutical compositions and uses thereof.

BACKGROUND OF THE INVENTION

Natural and synthetic alkaloids of opium (i.e., opioids) are useful as analgesics for the treatment of severe pain. Opioids target three types of endogenous opioid receptors: $\mu$-, $\delta$-, and $\kappa$-receptors. Many opioids, such as morphine, are $\mu$-receptor agonists that are highly efficacious analgesic compounds due to their activation of opioid receptors in the brain and central nervous system (CNS). Opioid receptors are, however, not only limited to the CNS, but may be found in other tissues throughout the body. These receptors located outside the CNS are referred to as peripheral receptors. A number of side effects associated with opioid use are caused by activation of these peripheral receptors. For example, administration of opioid agonists often results in intestinal dysfunction due to action of the opioid agonist upon the large number of receptors in the intestinal wall. Specifically, opioids are generally known to cause nausea and vomiting as well as inhibition of normal propulsive gastrointestinal function in animals, resulting in side effects such as constipation.

Opioid-induced side effects are a serious problem for patients being administered opioid analgesics for both short term and long term pain management. For instance, more than 250,000 terminal cancer patients each year take opioids, such as morphine, for pain relief, and about half of those patients experience severe constipation. In many situations the discomfort can be so great that the patients choose to forego the pain relief in order to avoid the constipation. In an effort to address this problem, certain opioid antagonist compounds that do not readily cross the blood-brain barrier have been tested for use in curbing opioid-induced side effects. For instance, the peripheral $\mu$-opioid antagonist compound, methylnaltrexone, and related compounds have been suggested for use in assuaging opioid-induced side effects. See for example, U.S. Pat. Nos. 5,972,954, 5,102,887, 4,861,781, and 4,719,215, which describe the use of methylnaltrexone and related compounds in controlling opioid-induced pruritus, nausea, and/or vomiting. Methylnaltrexone, however, is an experimental drug and is not commercially available. Unfortunately, most of the currently available opioid antagonists, such as the tertiary opioid antagonist, naloxone, are small molecules that not only possess antagonist activity at peripheral receptors associated with the intestine, but also possess antagonist activity at CNS receptors since they cross the blood-brain barrier. Consequently, many opioid antagonists interfere with the pain relief brought about by administration of opioid-based analgesics. Thus, at present, patients receiving opioid pain medications face the difficult choice of suffering burdensome adverse effects such as constipation or ineffective analgesia.

Thus, there is a need in the art for alternative compounds, or for approaches for modifying or improving upon existing compounds, that can reduce or eliminate opioid-induced side effects such as constipation, even when administered in high doses, without interfering with the pain-suppressing effects of the opioid.

SUMMARY OF THE INVENTION

The present invention is based upon the development of water-soluble, polymer-modified opioid antagonist compounds designed for the treatment of opioid-induced side effects such as constipation, while not reversing or impacting analgesia.

In one aspect, the present invention provides a polymer conjugate comprising a water-soluble and non-peptidic polymer covalently attached to an opioid antagonist.

Suitable polymers for covalent attachment to an opioid antagonist include poly(alkylene glycols), poly(oxyethylated polyol), poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphazene, polyoxazoline, poly(N-acryloylmorpholine), poly(acrylic acid), carboxymethyl cellulose, hyaluronic acid, hydroxypropylmethyl cellulose, and copolymers, terpolymers, and mixtures thereof. In one embodiment of the invention, the polymer is a polyethylene glycol. In an alternative embodiment, the polymer is polyacrylic acid.

The polymer portion of a conjugate of the invention may be linear, such as methoxy PEG, branched, or forked. In particular embodiments of the invention wherein the polymer is linear, the conjugate may incorporate a heterobifunctional or a homobifunctional polymer. A conjugate of a heterobifunctional polymer is one wherein one terminus of the polymer attached to the opioid antagonist and the other terminus is functionalized with a different moiety. A conjugate of a homobifunctional polymer possesses a structure wherein each end of a linear polymer is covalently attached to an opioid antagonist, typically by an identical linkage.

Exemplary opioid antagonists include buprenorphine, cyclazocine, cyclorphan, naloxone, N-methylnaloxone, naltrexone, N-methylnaltrexone, nalmephene, 6-amino-6-desoxo-naloxone, levallorphan, nalbuphine, naltrendol, naltrindole, nalorphine, norbinaltorphimine, oxilorphan, pentazocine, piperidine-N-alkylcarboxylate opioid antagonists, and opioid antagonist polypeptides. One particularly preferred opioid antagonist is naloxone or a derivative thereof, such as 6-amino-6-desoxo-naloxone.

In yet another embodiment, the polymer conjugate is covalently attached to the opioid antagonist by a hydrolytically stable linkage. Hydrolytically stable linkages include amide, amine, carbamate, ether, thioether, and urea-based linkages.

In one embodiment of the invention, the molecular weight of the polymer is less than about 5,000 daltons (Da).

In yet another embodiment, the molecular weight of the polymer is less than about 2,000 Da.

In yet an even more preferred embodiment, the molecular weight of the polymer is less than about 1,000 Da.

In yet another embodiment, the molecular weight of the polymer is less than about 800 Da.

In another aspect, the invention encompasses a pharmaceutical composition containing a polymer conjugate as described above in combination with a pharmaceutically acceptable carrier.

According to yet another aspect, the invention provides a method of treating at least one side effect of opioid administration, particularly side effects associated with the gastrointestinal system (e.g., nausea and constipation) by administering a conjugate of a water-soluble and non-peptidic polymer covalently attached to an opioid antagonist.

In one embodiment of the method, the conjugate is preferably administered conjointly with an opioid agonist, meaning the conjugate is administered at the same time as the opioid agonist or within a short period of time before or after administration of the opioid agonist. In yet a further embodiment of the method, the conjugate is administered orally.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

I. Definitions

The following terms as used herein have the meanings indicated.

As used in the specification, and in the appended claims, the singular forms "a", "an", "the", include plural referents unless the context clearly dictates otherwise.

The terms "functional group", "active moiety", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules. The term "active," when used in conjunction with a functional group, is intended to include those functional groups that react readily with electrophilic or nucleophilic groups on other molecules, in contrast to those groups that require strong catalysts or highly impractical reaction conditions in order to react (i.e., "non-reactive" or "inert" groups). For example, as would be understood in the art, the term "active ester" would include those esters that react readily with nucleophilic groups such as amines. Exemplary active esters include N-hydroxysuccinimidyl esters or 1-benzotriazolyl esters. Typically, an active ester will react with an amine in aqueous medium in a matter of minutes, whereas certain esters, such as methyl or ethyl esters, require a strong catalyst in order to react with a nucleophilic group. As used herein, the term "functional group" includes protected functional groups.

The term "protected functional group" or "protecting group" or "protective group" refers to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene, T. W., et al., *PROTECTIVE GROUPS IN ORGANIC SYNTHESIS*, 3rd ed., John Wiley & Sons, New York, N.Y. (1999).

The term "linkage" or "linker" (L) is used herein to refer to an atom or a collection of atoms used to link, preferably by one or more covalent bonds, interconnecting moieties such as two polymer segments or a terminus of a polymer and a reactive functional group present on a bioactive agent, such as an opioid antagonist. A linker of the invention may be hydrolytically stable or may include a physiologically hydrolyzable or enzymatically degradable linkage.

A "physiologically hydrolyzable" or "hydrolytically degradable" bond is a weak bond that reacts with water (i.e., is hydrolyzed) under physiological conditions. Preferred are bonds that have a hydrolysis half life at pH 8, 25° C. of less than about 30 minutes. The tendency of a bond to hydrolyze in water will depend not only on the general type of linkage connecting two central atoms but also on the substituents attached to these central atoms. Appropriate hydrolytically unstable or degradable linkages include but are not limited to carboxylate ester, phosphate ester, anhydrides, acetals, ketals, acyloxyalkyl ether, imines, orthoesters, peptides and oligonucleotides.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

An "enzymatically unstable" or degradable linkage is a linkage that can be degraded by one or more enzymes.

The term "polymer backbone" refers to the covalently bonded chain of repeating monomer units that form the polymer. The terms polymer and polymer backbone are used herein interchangeably. For example, the polymer backbone of PEG is $-CH_2CH_2O-(CH_2CH_2O)_n-CH_2CH_2$ where n typically ranges from about 2 to about 4000. As would be understood, the polymer backbone may be covalently attached to terminal functional groups or pendant functionalized side chains spaced along the polymer backbone.

The term "reactive polymer" refers to a polymer bearing at least one reactive functional group.

Unless otherwise noted, molecular weight is expressed herein as number average molecular weight ($M_n$), which is defined as $$\frac{\sum N_i M_i}{\sum N_i},$$

wherein Ni is the number of polymer molecules (or the number of moles of those molecules) having molecular weight Mi.

The term "alkyl", "alkenyl", and "alkynyl" refers to hydrocarbon chains typically ranging from about 1 to about 12 carbon atoms in length, preferably 1 to about 6 atoms, and includes straight and branched chains.

"Cycloalkyl" refers to a saturated or unsaturated cyclic hydrocarbon chain, including bridged, fused, or spiro cyclic compounds, preferably comprising 3 to about 12 carbon atoms, more preferably 3 to about 8.

The term "substituted alkyl", "substituted alkenyl", "substituted alkynyl" or "substituted cycloalkyl" refers to an alkyl, alkenyl, alkynyl or cycloalkyl group substituted with one or more non-interfering substituents, such as, but not limited to, C3-C8 cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g. chloro or bromo; phenyl; substituted phenyl, and the like.

"Alkoxy" refers to an —O—R group, wherein R is alkyl or substituted alkyl, preferably C1-C6 alkyl (e.g., methoxy or ethoxy).

"Aryl" means one or more aromatic rings, each of 5 or 6 core carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Substituted aryl" is aryl having one or more non-interfering groups as substituents. For substitutions on a phenyl ring, the substituents may be in any orientation (i.e., ortho, meta or para).

"Heteroaryl" is an aryl group containing from one to four heteroatoms, preferably N, O, or S, or a combination thereof, which heteroaryl group is optionally substituted at carbon or nitrogen atom(s) with C1-6 alkyl, —CF$_3$, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5-membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heteroaryls with three heteroatoms (e.g., 1,3,5-triazine); and 6-membered heteroaryls with four heteroatoms.

"Substituted heteroaryl" is heteroaryl having one or more non-interfering groups as substituents.

"Heterocycle" or "heterocyclic" means one or more rings of 5-12 atoms, preferably 5-7 atoms, with or without unsaturation or aromatic character and at least one ring atom which is not carbon. Preferred heteroatoms include sulfur, oxygen, and nitrogen. Multiple rings may be fused, as in quinoline or benzofuran.

"Substituted heterocycle" is heterocycle having one or more side chains formed from non-interfering substituents.

"Non-interfering substituents are those groups that, when present in a molecule, are typically non-reactive with other functional groups contained within the molecule.

Suitable non-interfering substituents or radicals include, but are not limited to, halo, C1-C10 alkyl, C2-C10 alkenyl, C2-C10 alkynyl, C1-C10 alkoxy, C7-C12 aralkyl, C7-C12 alkaryl, C3-C10 cycloalkyl, C3-C10 cycloalkenyl, phenyl, substituted phenyl, toluoyl, xylenyl, biphenyl, C2-C12 alkoxyalkyl, C7-C12 alkoxyaryl, C7-C12 aryloxyalkyl, C6-C12 oxyaryl, C1-C6 alkylsulfinyl, C1-C10 alkylsulfonyl, —(CH$_2$)$_m$—O—(C1-C10 alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)—(C1-C10 alkyl), —C(O)—(C1-C10 alkyl), C2-C10 thioalkyl, —C(O)O—(C1-C10 alkyl), —OH, —SO$_2$, =S, —COOH, —NR, carbonyl, —C(O)—(C1-C10 alkyl)-CF$_3$, —C(O)—CF$_3$, —C(O)NR$_2$, —(C1-C10 alkyl)-S—(C6-C12 aryl), —C(O)—(C6-C12 aryl), —(CH$_2$)$_m$—O—(CH$_2$)$_m$—O—(C1-C10 alkyl) wherein each m is from 1 to 8, —C(O)NR, —C(S)NR, —SO$_2$NR, —NRC(O)NR, —NRC(S)NR, salts thereof, and the like. Each R as used herein is H, alkyl or substituted alkyl, aryl or substituted aryl, aralkyl, or alkaryl.

"Heteroatom" means any non-carbon atom in a hydrocarbon analog compound. Examples include oxygen, sulfur, nitrogen, phosphorus, arsenic, silicon, selenium, tellurium, tin, and boron.

The term "drug", "biologically active molecule", "biologically active moiety" or "biologically active agent", when used herein means any substance which can affect any physical or biochemical properties of a biological organism, including but not limited to viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

"Polyolefinic alcohol" refers to a polymer comprising a polyolefin backbone, such as polyethylene, having multiple pendant hydroxyl groups attached to the polymer backbone. An exemplary polyolefinic alcohol is polyvinyl alcohol.

As used herein, "non-peptidic" refers to a polymer backbone substantially free of peptide linkages. However, the polymer backbone may include a minor number of peptide linkages spaced along the length of the backbone, such as, for example, no more than about 1 peptide linkage per about 50 monomer units.

"Polypeptide" refers to any molecule comprising a series of amino acid residues, typically at least about 10-20 residues, linked through amide linkages (also referred to as peptide linkages) along the alpha carbon backbone. While in some cases the terms may be used synonymously herein, a polypeptide is a peptide typically having a molecular weight up to about 10,000 Da, while peptides having a molecular weight above that are commonly referred to as proteins. Modifications of the peptide side chains may be present, along with glycosylations, hydroxylations, and the like. Additionally, other non-peptidic molecules, including lipids and small drug molecules, may be attached to the polypeptide.

By "residue" is meant the portion of a molecule remaining after reaction with one or more molecules. For example, an opioid antagonist residue in the polymer conjugate of the invention is the portion of an opioid antagonist remaining following covalent linkage to a polymer backbone.

"Oligomer" refers to short monomer chains comprising 2 to about 10 monomer units, preferably 2 to about 5 monomer units.

The term "conjugate" is intended to refer to the entity formed as a result of covalent attachment of a molecule, e.g., a biologically active molecule such as an opioid antagonist, to a reactive polymer molecule, preferably poly(ethylene glycol).

"Bifunctional" in the context of a polymer of the invention refers to a polymer possessing two reactive functional groups which may be the same or different.

"Multifunctional" in the context of a polymer of the invention means a polymer having 3 or more functional groups attached thereto, where the functional groups may be the same or different. Multifunctional polymers of the invention will typically comprise from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups attached to the polymer backbone.

II. Polymer Conjugates of Opioid Antagonists

As described generally above, the polymer conjugates of the invention comprise a water-soluble and non-peptidic polymer covalently attached to an opioid antagonist. The polymer conjugates of the invention are useful for the treatment of one or more side effects of opioid analgesic administration, such as nausea, pruritus or constipation. The conjugates of the invention typically comprise a polymer having a molecular weight selected such that the conjugate either i) does not pass to any appreciable extent through the intestinal wall and into the bloodstream, so as to increase the localized concentration of polymer conjugate in the intestine and promote binding to opioid receptors in the intestinal wall, and/or ii) does not pass through the blood-brain barrier and into the CNS. According to one feature of the invention, upon administration, the polymer conjugate is retained within the gastrointestinal system and acts directly in the gut, or at least outside of the CNS, to reduce the likelihood of the opioid antagonist interfering with the analgesic effects of the opioid compound. In this manner, the polymer conjugates of the invention are capable of treating the common side effects of opioid use by selectively reacting with peripheral receptors without adversely impacting the analgesic effect of the opioid.

So, in essence, covalent attachment of the polymer to the opioid antagonist can increase the resistance of the conjugate to both intestinal barrier transport (e.g., into the circulation) and blood-brain barrier transport as compared to the unmodified opioid antagonist, thereby (i) preventing the opioid antagonist from interfering with the pain relief provide by the opioid and (ii) improving the effectiveness of the unmodified opioid antagonist.

For the most effective treatment of opioid-induced constipation stemming from interaction of the opioid with opioid receptors within the intestinal wall, it is preferable to select a polymer molecular weight that prevents or at least significantly reduces penetration of the polymer conjugate through the intestinal wall and into the bloodstream. Preferably, the molecular weight of the polymer is selected so as not to impede penetration of the polymer conjugate into the mucosal membrane of the intestinal barrier. As would be understood, the mucosal membrane is the primary intestinal barrier to potentially harmful antigens and bacteria and comprises epithelial cells that secrete, and are coated with, a layer of mucus about 2 mm thick, which adheres tightly to the cell membranes. The mucus lubricates the epithelial cell surfaces and prevents mechanical damage by the stomach contents. Although not bound by any particular theory, penetration into the mucosal membrane is believed to promote interaction between the polymer conjugate of the invention and the peripheral opioid receptors in the intestinal wall. Thus, the conjugates of the invention are preferably designed to achieve a balance of factors, such as (i) maintaining the antagonist activity of the opioid antagonist, (ii) penetrating the mucosal barrier of the intestine while not crossing to a significant extent from the intestine into the bloodstream, and (iii) if present in the general circulation, exhibiting the inability to cross the blood-brain barrier to any significant degree.

Typically, the number average molecular weight of the polymer portion of a polymer conjugate of the invention is less than about 5,000 daltons (Da), and more preferably is less than about 2,000 Da. In an even more preferred embodiment of the invention, the polymer possesses a molecular weight of about 1,000 Da or less, or of about 800 Da or less. In turning now to ranges of molecular weights for the polymer portion of the conjugate, the molecular weight range is generally from about 100 Da to about 2,000 Da, preferably about 100 Da to about 1,000 Da, more preferably about 100 Da to about 800 Da, or from about 100 Da to about 500 Da. Polymer backbones having a number average molecular weight of about 100 Da, about 200 Da, about 300 Da, about 400 Da, about 500 Da, about 550 Da, about 600 Da, about 700 Da, about 800 Da, about 900 Da and about 1,000 Da are particularly preferred. The polymers of the invention are hydrophilic in nature, thereby imparting hydrophilicity to the resulting conjugates and making them unable to cross the blood-brain barrier to a significant extent.

To reduce the possibility of deactivation of the antagonist activity of the opioid antagonist compound and to keep the total molecular weight of the polymer backbone portion of the conjugate within the preferred range, it is sometimes preferable to only attach a single polymer backbone to the opioid antagonist molecule, or, if employing a branched polymer, to utilize a polymer at the lower end of the preferred molecular weight ranges described above. Alternatively, a linear or forked polymer having two opioid antagonist molecules attached may be used to achieve the desired balance of activity and penetration characteristics.

The linkage between the polymer backbone and the opioid antagonist is preferably hydrolytically stable so that the opioid antagonist is not released from the polymer following administration to a patient. Release of the opioid antagonist in vivo could lead to a loss in analgesic effect of the opioid compound due to passage of the released opioid antagonist into the CNS. Representative linkages for connecting the opioid antagonist and the polymer include ether, amide, urethane (also known as carbamate), amine, thioether (also known as sulfide), and urea (also known as carbamide) linkages. The particular linkage and linkage chemistry employed will depend upon the subject opioid antagonist, functional groups within the molecule available either for attachment to a polymer or conversion to a suitable attachment site, the presence of additional functional groups within the molecule, and the like, and can be readily determined by one skilled in the art based upon the guidance presented herein.

The polymer conjugates of the invention maintain at least a measurable degree of specific opioid antagonist activity. That is to say, a polymer conjugate in accordance with the invention will possesses anywhere from about 1% to about 100% or more of the specific activity of the unmodified parent opioid antagonist compound. Such activity may be determined using a suitable in-vivo or in-vitro model, depending upon the known activity of the particular opioid antagonist parent compound. For example, a hot plate or tail flick analgesia assay can be used to assess the level of antagonist activity of the polymer conjugates of the invention (See, for example, Tulunay, et al., *J Pharmacol Exp Ther* 1974; 190:395-400; Takahashi, et al., *Gen Pharmacol* 1987; 18(2):201-3; Fishman, et al, *Pharmacology* 1975; 13(6):513-9). In general, a polymer conjugate of the invention will possess a specific activity of at least about 2%, 5%, 10%, 15%, 25%, 30%, 40%, 50%, 60%, 80%, 90% or more relative to that of the unmodified parent opioid antagonist, when measured in a suitable model, such as those well known in the art. Preferably, a conjugate of the invention will maintain at least 50% or more of the opioid antagonist activity of the unmodified parent compound.

In addition to maintaining at least a portion of the opioid antagonist activity of the parent opioid antagonist compound, the polymer conjugates of the invention also exhibit high levels of activity with respect to peripheral opioid receptors in gastrointestinal tissue, while exhibiting substantially no activity with respect to opioid receptors in the CNS. The term "substantially no CNS activity", as used herein, means the polymer conjugates of the invention cause less than about a 25% reduction in the analgesic effect of the opioid agonist, which can be measured, for example, using a tail flick or hot plate analgesia assay as described above. In preferred embodiments, the polymer conjugates of the invention cause less than about 20% reduction in the analgesic effect of the opioid agonist, more preferably less than about 15% reduction, or even less than about 10% or less than about 5% reduction. A reduction of analgesic effect of about 0% (i.e., no reduction in analgesia) is most preferred.

A polymer conjugate of the invention will typically comprise a water-soluble and non-peptidic polymer, such as poly(ethylene glycol), covalently attached to an opioid antagonist and having a generalized structure as shown below.

POLY-X-A<sub>o</sub>        Formula I wherein:

POLY is a water-soluble and non-peptidic polymer;

X is a linkage, preferably a hydrolytically stable linkage covalently attaching the polymer to the opioid antagonist; and A<sub>o</sub> is the opioid antagonist.

In one preferred embodiment, the conjugate of Formula I has the structure:

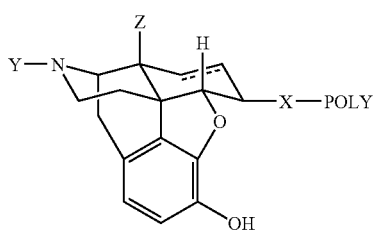

Formula Ia wherein:

Y is C1-C6 alkyl, substituted C1-C6 alkyl, C3-C6 cycloalkyl, substituted C1-C6 cycloalkyl, C2-C6 alkenyl, substituted C2-C6 alkenyl, C2-C6 alkynyl, substituted C2-C6 alkynyl, aryl, substituted aryl, heteroaryl, substituted heteroaryl, heterocycle, and substituted heterocycle;

Z is H or OH;

the dashed line indicates an optional double bond; and

X and POLY are as defined above.

In another embodiment, the conjugate of Formula I has the structure:

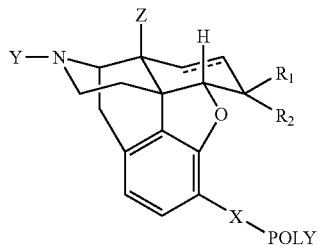

Formula Ib wherein:

$R_1$ and $R_2$ are each independently hydrogen or OH, or together form $=CH_2$ or $=O$; and X, Y, Z, the dashed line, and POLY are as defined above.

In either Formula Ia or Formula Ib, preferred Y groups include C1-C6 alkyl, substituted C1-C6 alkyl (e.g., C1-C6 alkyl substituted with C1-C6 cycloalkyl), C2-C6 alkenyl (e.g., allyl), substituted C2-C6 alkenyl (e.g., chloroallyl), C2-C6 alkynyl (e.g., propargyl), substituted C2-C6 alkynyl, C3-C6 cycloalkyl, and substituted C3-C6 cycloalkyl.

As would be understood, the particular Y, Z, $R_1$, and $R_2$ groups employed will depend on the specific opioid antagonist used to form the polymer conjugate of the invention. Preferred opioid antagonists include naloxone or derivatives thereof (i.e., Y=allyl, Z=OH, $R_1$ and $R_2$ together form=O, no optional double bond), nalbuphine or derivatives thereof (i.e., Y=(cyclobutyl)methyl, Z=OH, $R_1$=H, $R_2$=OH, no optional double bond), nalmephene or derivatives thereof (i.e., Y=(cyclopropyl)methyl, Z=OH, $R_1$ and $R_2$ together form=CH<sub>2</sub>, no optional double bond), naltrexone or derivatives thereof (i.e., Y=(cyclopropyl)methyl, Z=OH, $R_1$ and $R_2$ together form =O, no optional double bond), and nalorphine or derivatives thereof (Y=allyl, Z=H, $R_1$=H, $R_2$=OH, optional double bond present).

The polymer conjugates of the invention may be administered per se or in the form of a pharmaceutically acceptable salt, and any reference to the polymer conjugates of the invention herein is intended to include pharmaceutically acceptable salts. If used, a salt of the polymer conjugate should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the polymer conjugate with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulphonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group.

A. Polymer Backbone

In general, the water soluble and non-peptidic polymer portion of the conjugate should be non-toxic and biocompatible, meaning that the polymer is capable of coexistence with living tissues or organisms without causing harm. When referring to a polymer conjugate, it is to be understood that the polymer can be any of a number of water soluble and non-peptidic polymers, such as those described herein as suitable for use in the present invention. Preferably, poly(ethylene glycol) (PEG) is the polymer backbone. The term PEG includes poly(ethylene glycol) in any of a number of geometries or forms, including linear forms (e.g., alkoxy PEG or bifunctional PEG), branched or multi-arm forms (e.g., forked PEG or PEG attached to a polyol core), pendant PEG, or less preferably, PEG with degradable linkages therein, to be more fully described below.

In its simplest form, PEG has the formula $$-CH_2CH_2O-(CH_2CH_2O)_n-CH_2CH_2-\qquad\text{Formula II}$$

wherein n is from about 2 to about 45, typically from about 2 to about 20.

As described above, end-capped polymers, meaning polymers having at least one terminus capped with a relatively inert group (e.g., an alkoxy group), can be used as a polymer of the invention. For example, methoxy-PEG-OH, or MPEG in brief, is a form of PEG wherein one terminus of the polymer is a methoxy group, while the other terminus is a hydroxyl group that is subject to ready chemical modification. The structure of mPEG is given below.

$$CH_3O-(CH_2CH_2O)_n-CH_2CH_2-OH\qquad\text{Formula III}$$

wherein n is as described above.

Multi-armed or branched PEG molecules, such as those described in U.S. Pat. No. 5,932,462, which is incorporated by reference herein in its entirety, can also be used as the PEG polymer. Generally speaking, a multi-armed or branched polymer possesses two or more polymer "arms" extending from a central branch point (e.g., C in the structure below) that is covalently attached, either directly or indirectly via intervening connecting atoms, to one active moiety such as an opioid antagonist. For example, an exemplary branched PEG polymer can have the structure:

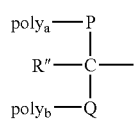

Formula IV wherein:

poly$_a$ and poly$_b$ are PEG backbones, such as methoxy poly (ethylene glycol);

R" is a nonreactive moiety, such as H, methyl or a PEG backbone; and

P and Q are nonreactive linkages. In a preferred embodiment, the branched PEG polymer is methoxy poly(ethylene glycol) disubstituted lysine.

The PEG polymer may alternatively comprise a forked PEG. Generally speaking, a polymer having a forked structure is characterized as having a polymer chain attached to two or more active agents via covalent linkages extending from a hydrolytically stable branch point in the polymer. An example of a forked PEG is represented by PEG-YCHZ$_2$, where Y is a linking group and Z is an activated terminal group, such as an aldehyde group, for covalent attachment to an opioid antagonist, linked to CH by a chain of atoms of defined length. International Application No. PCT/US99/05333, the contents of which are incorporated by reference herein, discloses various forked PEG structures capable of use in the present invention. The chain of atoms linking the Z functional groups to the branching carbon atom serve as a tethering group and may comprise, for example, an alkyl chain, ether linkage, ester linkage, amide linkage, or combinations thereof.

The PEG polymer may comprise a pendant PEG molecule having reactive groups, such as carboxyl, covalently attached along the length of the PEG backbone rather than at the end of the PEG chain. The pendant reactive groups can be attached to the PEG backbone directly or through a linking moiety, such as an alkylene group.

In addition to the above-described forms of PEG, the polymer can also be prepared with one or more weak or degradable linkages in the polymer backbone, including any of the above described polymers, although this embodiment is somewhat less preferred for the conjugates of the present invention. For example, PEG can be prepared with ester linkages in the polymer backbone that are subject to hydrolysis. As shown below, this hydrolysis results in cleavage of the polymer into fragments of lower molecular weight:

$$-PEG-CO_2-PEG-+H_2O\rightarrow-PEG-CO_2H+HO-PEG-$$

Other hydrolytically degradable linkages, useful as a degradable linkage within a polymer backbone, include carbonate linkages; imine linkages resulting, for example, from reaction of an amine and an aldehyde (see, e.g., Ouchi et al., Polymer Preprints, 38(1):582-3 (1997), which is incorporated herein by reference.); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

It is understood by those skilled in the art that the term poly(ethylene glycol) or PEG represents or includes all the above forms of PEG.

As noted previously above, any of a variety of monofunctional, bifunctional or multifunctional polymers that are non-peptidic and water-soluble can also be used to form a conjugate in accordance with the present invention. The polymer backbone can be linear, or may be in any of the above-described forms (e.g., branched, forked, and the like). Examples of suitable polymers include, but are not limited to, other poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(acrylic acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. In addition to PEG, poly(acrylic acid) is a preferred polymer species because it has the known property of adherence to mucosa, which may offer advantages in binding of the conjugated antagonist to membrane surface receptors.

B. Linkage Between Polymer Backbone and Opioid Antagonist

The linkage between the opioid antagonist and the polymer backbone (i.e., X in Formula I) results from the reaction of a reactive functional group of the polymer with a functional group on the opioid antagonist molecule. The specific linkage will depend on the structure of the functional groups utilized, and will typically be governed by the functional groups contained in the opioid antagonist molecule. For example, an amide linkage can be formed by reaction of a polymer having a terminal carboxylic acid group, or an active ester thereof, with an opioid antagonist having an amine group. Alternatively, a sulfide linkage can be formed by reaction of a polymer terminated with a thiol group with an opioid antagonist bearing a hydroxyl group. In another embodiment, an amine linkage is formed by reaction of an amino-terminated polymer with an opioid antagonist bearing a hydroxyl group. The particular coupling chemistry employed will depend upon the structure of the opioid antagonist, the potential presence of multiple functional groups within the opioid antagonist, the need for protection/deprotection steps, chemical stability of the molecule, and the like, and will be readily determined by one skilled in the art. Illustrative linking chemistry useful for preparing the polymer conjugates of the invention can be found, for example, in Wong, S. H., (1991), "*Chemistry of Protein Conjugation and Crosslinking*", CRC Press, Boca Raton, Fla. and in Brinkley, M. (1992) "*A Brief Survey of Methods for Preparing Protein Conjugates with Dyes, Haptens, and Crosslinking Reagent's*, in *Bioconjug. Chem.*, 3, 2013.

The linkage is preferably hydrolytically stable to prevent release of the opioid antagonist after administration to the patient, thereby reducing the possibility of transport of the antagonist through the intestinal barrier and into the bloodstream. Once in the bloodstream, there is an increased possibility of the antagonist passing through the blood-brain barrier and negatively impacting the analgesic effect of the opioid, depending of course on the particulars of the particular opioid antagonist. Exemplary hydrolytically stable linkages include amide, amine, carbamate, ether, thioether, and urea.

The overall X linkage is intended to encompass any linkage between the polymer and the opioid antagonist molecule having an overall length of from 1 to about 20 atoms, preferably 1 to about 10 atoms.

In Formula Ia above, the X linkage is preferably a secondary amine or amide linkage. In one embodiment of Formula Ia, X has the formula —NH—$(CHR_O)_m$—O— or —NH—C(O)—$(CHR_O)_n$—O—, wherein m is 1-12, preferably 1-4 (i.e., 1, 2, 3, or 4) and each $R_O$ is independently H or C1-C6 alkyl (e.g., methyl or ethyl). In Formula Ib above, the X linkage is preferably a heteroatom, such as an ether or thioether linkage (i.e., X=O or S).

C. Opioid Antagonists

As defined herein, an "opioid antagonist" is any molecule that blocks the action of an opioid agonist at one or more opioid receptor types, including so-called "agonist-antagonist" molecules that act as an antagonist for one opioid receptor type and an agonist for another receptor type (e.g., nalorphine or pentazocine). The opioid antagonist preferably exhibits no agonist activity for any opioid receptor type and preferably exhibits antagonist activity for μ-receptors. Many opioid antagonists are structurally similar to the closest agonist analogue, with the exception of a larger hydrocarbon group attached to the $N_{17}$ position. For example, nalorphine is structurally identical to morphine with the exception of replacement of the $N_{17}$ methyl group of morphine with an allyl group. Suitable opioid antagonists include, but are not limited to, buprenorphine, cyclazocine, cyclorphan, naloxone, N-methylnaloxone, naltrexone, N-methylnaltrexone, nalmephene, 6-amino-6-desoxo-naloxone, levallorphan, nalbuphine, naltrendol, naltrindole, nalorphine, nor-binaltorphimine, oxilorphan, pentazocine, piperidine-N-alkylcarboxylate opioid antagonists such as those described in U.S. Pat. Nos. 5,159,081; 5,250,542; 5,270,328; and 5,434,171 (all of which are incorporated by reference herein), opioid antagonist polypeptides (such as those described by R. J. Knapp, L. K. Vaughn, and H. I. Yamamura in "The Pharmacology of Opioid Peptides", L. F. Tseng, Ed., p. 15, Harwood Academic Publishers, (1995)), and derivatives or mixtures thereof.

D. Method of Forming Polymer Conjugates of Opioid Antagonists

The polymer conjugate of the invention can be formed using known techniques for covalent attachment of an activated polymer, such as an activated PEG, to a biologically active agent (See, for example, *POLY(ETHYLENE GLYCOL) CHEMISTRY AND BIOLOGICAL APPLICATIONS*, American Chemical Society, Washington, D.C. (1997)). The general method involves selection of a reactive polymer bearing a functional group suitable for reaction with a functional group of the opioid antagonist molecule and reaction of the reactive polymer with the opioid antagonist in solution to form a covalently-bound conjugate.

Selection of the functional group of the polymer will depend, in part, on the functional group on the opioid antagonist molecule. The functional group of the polymer is preferably chosen to result in formation of a hydrolytically stable linkage between the opioid antagonist and the polymer. A polymer of the invention suitable for coupling to an opioid antagonist molecule will typically have a terminal functional group such as the following: N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al., Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461). All of the above references are incorporated herein by reference.

In a particular embodiment exemplified in Examples 1-4, the ketone group of naloxone or naltrexone is subjected to reductive amination to form an amino derivative of naloxone or naltrexone using methodology described by Jiang, et al. (*J. Med. Chem.*, 1977, 20:1100-1102). The amino derivative is then reacted with (i) an aldehyde-terminated polymer in the presence of a reducing agent to form a secondary amine linkage or (ii) an active ester-terminated polymer to form an amide linkage.

The polymer conjugate product may be purified and collected using methods known in the art for biologically active conjugates of this type. Typically, the polymer conjugate is isolated by precipitation followed by filtration and drying.

E. Exemplary Conjugate Structures

More specific structural embodiments of the conjugates of the invention will now be described, all of which are intended to be encompassed by the structure of Formula I above. The specific structures shown below are presented as exemplary structures only, and are not intended to limit the scope of the invention.

An embodiment of a linear polymer of the invention can be structurally represented as shown below:

$$R\text{-POLY-X-}A_o \qquad \text{Formula V}$$

wherein POLY is a water soluble and non-peptidic polymer backbone, R is a capping group or a functional group, and X and $A_o$ are as defined above. In a preferred embodiment, R is methoxy, POLY is poly(ethylene glycol), X is a hydrolytically stable linkage such as amide, amine, carbamate, sulfide, ether, thioether, or urea, and $A_o$ has the structure shown in Formula Ia or Formula Ib above.

The R group can be a relatively inert capping group, such as alkoxy (e.g., methoxy or ethoxy), alkyl, benzyl, aryl, or aryloxy (e.g., benzyloxy). Alternatively, the R group can be a functional group capable of readily reacting with a functional group on a biologically active molecule such as another opioid antagonist. Exemplary functional groups include hydroxyl, active ester (e.g. N-hydroxysuccinimidyl ester or 1-benzotriazolyl ester), active carbonate (e.g. N-hydroxysuccinimidyl carbonate and 1-benzotriazolyl carbonate), acetal, aldehyde, aldehyde hydrate, alkenyl, acrylate, methacrylate, acrylamide, active sulfone, amine, hydrazide, thiol, carboxylic acid, isocyanate, isothiocyanate, maleimide, vinylsulfone, dithiopyridine, vinylpyridine, iodoacetamide, epoxide, glyoxal, dione, mesylate, tosylate, or tresylate.

In a homobifunctional embodiment of Formula V, R has the structure —X-$A_o$, wherein X and $A_o$ are as defined above.

One example of a multi-arm embodiment of the polymer conjugate of the invention has the structure:

$$R'\text{[-POLY-X-}A_o]_y \qquad \text{Formula VI}$$

wherein each POLY is a water soluble and non-peptidic polymer backbone, R' is a central core molecule, y is from about 3 to about 100, preferably 3 to about 25, and X and $A_o$ are as defined above. The core moiety, R', is a residue of a molecule selected from the group consisting of polyols, polyamines, and molecules having a combination of alcohol and amine groups. Specific examples of central core molecules include glycerol, glycerol oligomers, pentaerythritol, sorbitol, and lysine.

The central core molecule is preferably a residue of a polyol having at least three hydroxyl groups available for polymer attachment. A "polyol" is a molecule comprising a plurality of available hydroxyl groups. Depending on the desired number of polymer arms, the polyol will typically comprise 3 to about 25 hydroxyl groups. The polyol may include other protected or unprotected functional groups as well without departing from the invention. Although the spacing between hydroxyl groups will vary from polyol to polyol, there are typically 1 to about 20 atoms, such as carbon atoms, between each hydroxyl group, preferably 1 to about 5. Preferred polyols include glycerol, reducing sugars such as sorbitol, pentaerythritol, and glycerol oligomers, such as hexaglycerol. A 21-arm polymer can be synthesized using hydroxypropyl-β-cyclodextrin, which has 21 available hydroxyl groups. The particular polyol chosen will depend on the desired number of hydroxyl groups needed for attachment to the polymer arms. In this particular embodiment, as the number of polymer arms in the conjugate is increased, the molecular weight or number of monomer subunits of each of the polymer arms will preferably decrease in order to keep within the preferred molecular weight ranges for a conjugate in accordance with the invention.

III. Pharmaceutical Compositions Including a Polymer Conjugate of the Invention The invention provides pharmaceutical formulations or compositions, both for veterinary and for human medical use, which comprise one or more polymer conjugates of the invention or a pharmaceutically acceptable salt thereof, with one or more pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions of the invention may also include polymeric excipients/additives or carriers, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), and in "Handbook of Pharmaceutical Excipients", Third Ed., Ed. A. H. Kibbe, Pharmaceutical Press, 2000.

The conjugates of the invention may be formulated in compositions including those suitable for oral, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the active agent or compound (i.e., the polymer conjugate) into association with a carrier that constitutes one or more accessory ingredients. In general, the compositions are prepared by bringing the active compound into association with a liquid carrier to form a solution or a suspension, or alternatively, bring the active compound into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter.

The amount of polymer conjugate in the formulation will vary depending upon the specific opioid antagonist employed, its activity in conjugated form, the molecular weight of the conjugate, and other factors such as dosage form, target patient population, and other considerations, and will generally be readily determined by one skilled in the art. The amount of conjugate in the formulation will be that amount necessary to deliver a therapeutically effective amount of opioid antagonist to a patient in need thereof to achieve at least one of the therapeutic effects associated with the opioid antagonist, e.g., relief of one or more side effects of opioid use, such as nausea, constipation or pruritus. In practice, this will vary widely depending upon the particular conjugate, its activity, the severity of the condition to be treated, the patient population, the stability of the formulation, and the like. Compositions will generally contain anywhere from about 1% by weight to about 99% by weight conjugate, typically from about 2% to about 95% by weight conjugate, and more typically from about 5% to 85% by weight conjugate, and will also depend upon the relative amounts of excipients/additives contained in the composition. More specifically, the composition will typically contain at least about one of the following percentages of conjugate: 2%, 5%, 10%, 20%, 30%, 40%, 50%, 60%, or more by weight.

Compositions of the present invention suitable for oral administration may be presented as discrete units such as capsules, cachets, tablets, lozenges, and the like, each containing a predetermined amount of the active agent as a powder or granules; or a suspension in an aqueous liquor or non-aqueous liquid such as a syrup, an elixir, an emulsion, a draught, and the like.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised with a suitable carrier may be made by molding in a suitable machine.

A syrup may be made by adding the active compound to a concentrated aqueous solution of a sugar, for example sucrose, to which may also be added any accessory ingredient(s). Such accessory ingredients may include flavorings, suitable preservatives, an agent to retard crystallization of the sugar, and an agent to increase the solubility of any other ingredient, such as polyhydric alcohol, for example, glycerol or sorbitol.

Formulations suitable for parenteral administration conveniently comprise a sterile aqueous preparation of the conjugate, which can be formulated to be isotonic with the blood of the recipient.

Nasal spray formulations comprise purified aqueous solutions of the active agent with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical formulations. The addition of other accessory ingredients as noted above may be desirable.

Pharmaceutical formulations are also provided which are suitable for administration as an aerosol, by inhalation. These formulations comprise a solution or suspension of the desired polymer conjugate or a salt thereof. The desired formulation may be placed in a small chamber and nebulized. Nebulization may be accomplished by compressed air or by ultrasonic energy to form a plurality of liquid droplets or solid particles comprising the conjugates or salts thereof.

IV. Method of Using the Polymer Conjugates

The polymer conjugates of the invention can be used to treat any condition responsive to opioid antagonists in any animal, particularly in mammals, including humans. A preferred condition for treatment is any side effect associated with opioid analgesic use, such as nausea, constipation, or pruritus. Alternatively, the polymer conjugate of the invention can be used prophylactically to prevent the side effects of opioid use. The method of treatment comprises administering to the mammal a therapeutically effective amount of a composition or formulation containing a polymer conjugate of an opioid antagonist as described above. The therapeutically effective dosage amount of any specific conjugate will vary somewhat from conjugate to conjugate, patient to patient, and will depend upon factors such as the condition of the patient, the activity of the particular opioid antagonist employed, and the route of delivery. As would be understood, if a polymer conjugate of an opioid antagonist has reduced antagonist activity as compared to the unconjugated parent molecule, higher doses can be used to offset the reduced activity. As a general proposition, a dosage from about 0.5 to about 100 mg/kg body weight, preferably from about 1.0 to about 20 mg/kg, will have therapeutic efficacy. When administered conjointly with other pharmaceutically active agents, even less of the polymer conjugate may be therapeutically effective.

The polymer conjugate may be administered once or several times a day. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals.

The polymer conjugate can be administered conjointly with the opioid agonist, meaning the polymer conjugate and the opioid agonist are administered at the same time or the opioid agonist and the polymer conjugate are both administered within a short time interval in any order. Preferably, the opioid agonist and the polymer conjugate are administered at the same time or within about an hour apart, more preferably within about 30 minutes apart, even more preferably within about 15 minutes apart (in any order). As would be understood in the art, if the opioid agonist and the polymer conjugate are administered conjointly, the two therapeutic agents can be administered in the same formulation (i.e., in the same dosage unit).

Oral delivery is the preferred route of administration for both the opioid agonist and the polymer conjugate of the invention. However, both therapeutic agents could be delivered using other routes and different routes of administration could be used for each therapeutic agent. For example, the opioid agonist could be delivered intravenously and the polymer conjugate of the invention could be delivered orally.

As used herein, an "opioid agonist" is any natural or synthetic alkaloid of opium that activates one or more opioid receptor types, including partial agonists (i.e., compounds exhibiting activity against less than all opioid receptor types) and agonist-antagonists (i.e., compounds exhibiting agonist activity at one receptor type and antagonist activity at another receptor type). The opioid agonist can be a natural alkaloid such as a penanthrene (e.g., morphine) or benzylisoquinoline (e.g., papaverine), a semi-synthetic derivative (e.g., hydromorphone), or any of various classes of synthetic derivatives (e.g., phenylpiperidines, benzmorphans, priopionanilides, and morphinans). Exemplary opioid agonists include alfentanil, bremazocine, buprenorphine, butorphanol, codeine, cyclazocine, dezocine, diacetylmorphine (i.e., heroin), dihydrocodeine, fentanyl, hydrocodone, hydromorphone, levorphanol, meperidine (pethidine), methadone, morphine, nalbuphine, noscapine, oxycodone, oxymorphone, papaverine, pentazocine, pethidine, phenazocine, propiram, propoxyphene, sufentanil, thebaine and tramadol. Preferably, the opioid agonist is selected from the group consisting of morphine, codeine, oxycodone, hydrocodone, dihydrocodeine, propoxyphene, fentanyl, and tramadol.

V. EXAMPLES

The following examples are given to illustrate the invention, but should not be considered in limitation of the invention. For example, although mPEG is used in the examples to illustrate the invention, other forms of PEG and similar polymers that are useful in the practice of the invention are encompassed by the invention as discussed above.

All PEG reagents referred to in the appended examples are available from Shearwater Corporation of Huntsville, Ala. All $^1$HNMR data was generated by a 300 or 400 MHz NMR spectrometer manufactured by Bruker.

Examples 1-4 illustrate methods of forming polymer conjugates using mPEG as the polymer backbone and 6-amino-6-desoxo-naloxone as the opioid antagonist. Examples 1 and 3 illustrate the formation of a hydrolytically stable secondary amine linkage between the polymer backbone and the opioid antagonist. Examples 2 and 4 illustrate the formation of a hydrolytically stable amide linkage between the polymer backbone and the opioid antagonist. Note that 6-amino-6-desoxo-naloxone exists as a mixture of two epimers, alpha and beta. Both epimers are believed to be active and, thus, a mixture of the two epimers can be used. However, although not exemplified below, the two epimers can be separated using separation methods known in the art.

Example 1

Preparation of 6-mPEG (550 Da)—NH-6-desoxo-naloxone (Mixture of 6-epimers)

A. Synthesis of 6-amino-6-desoxo-naloxone (Mixture of 6-amino epimers)

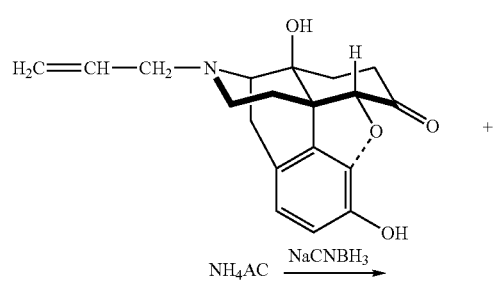

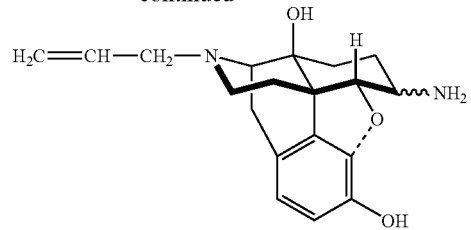

Naloxone was subjected to reductive amination by methods similar to those of Jiang, et al. (J. Med. Chem., 20: 1100-1102, 1977). To a mixture of naloxone (7.4 g) and ammonium acetate (15.4 g) dissolved in methanol (50 ml) under nitrogen was added a methanolic solution (40 ml) of NaCNBH$_3$ (1.4 g). The resulting solution was adjusted to pH 7.0 with concentrated HCl, stirred for 20 hours, and acidified to pH 1 with addition of concentrated HCl. After removal of the solvent and dissolution of the residue in water, the aqueous solution was extracted with chloroform to remove the water-insoluble material and was then adjusted to pH 9.0 with Na$_2$CO$_3$. The mixture was saturated with NaCl and extracted with CHCl$_3$. The CHCl$_3$ phase was dried with Na$_2$SO$_4$ and evaporated to dryness. The oily residue was dissolved in 60 ml of methanol, acidified to pH 1.0 with concentrated HCl and allowed to stand overnight at 4° C. The solvent was evaporated to dryness and the residue dried under vacuum.

Yield: 7.13 g. $^1$H nmr (DMSO-d$_6$): δ 6.56 ppm and δ 6.52 ppm (1H each, two doublets, aromatic H), δ 5.83 ppm (1H multi. olefinic H), δ 5.18 ppm (2H multi. olefinic H), δ 5.01 ppm (1H singlet,), δ 4.76 ppm (1H singlet).

B. Preparation of 6-mPEG (550 Da)-NH-6-desoxo-naloxone (Mixture of 6-epimers)

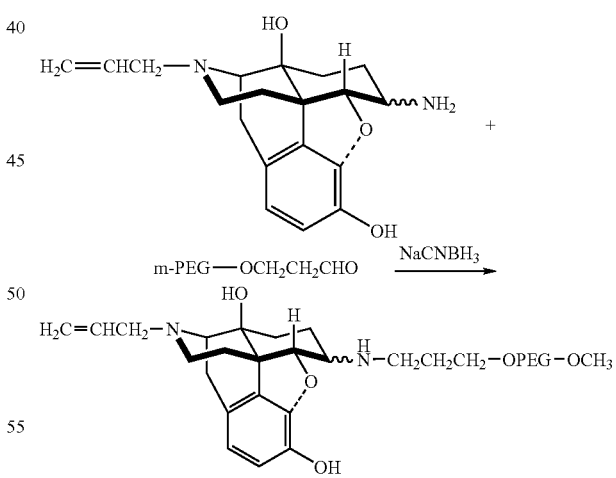

To a mixture of mPEG-550-aldehyde (Shearwater Corporation, M.W. 550 Da 2.0 g, 3.3 mmol) and 6-NH$_2$-naloxone.2HCl (1.6 g, 4.0 mmol) (from Step A) dissolved in deionized water (25 ml) under argon was added an aqueous solution (20 ml) of NaCNBH$_3$ (0.15 g, 2.4 mmol). The resulting solution was stirred at room temperature under argon overnight (18 h). The solution was then diluted with DI water (350 ml), acidified with concentrated HCl to pH 1 and washed with CHCl$_3$ (3×150 ml) to remove unbound PEG. To the aqueous phase was added Na₂HPO₄ (6.0 g, 42 mmol, 100 mM), the pH adjusted to 6.0 with NaOH and the resulting solution extracted with CHCl₃ (3×200 ml). The CHCl₃ extracts were combined, washed with a pH 6.5 phosphate buffer (100 mM, 3×200 ml), dried over anhydrous Na₂SO₄, evaporated under vacuum and dried in vacuo for 2 days. The pure conjugate was obtained as a light yellow liquid (1.3 g, 1.4 mmol, 42% yield).

$^1$H NMR (CDCl₃): δ 6.51-6.74 (2H, multiplet, aromatic protons of naloxone); 5.72-5.85 (1H, multiplet, olefinic proton of naloxone); 5.16 (2H, triplet, olefinic protons of naloxone); 4.76 and 4.46 (1H, two doublet, C₅ proton of α and β naloxone); 3.64 (~57H, multiplet, PEG); 3.38 (3H, singlet, methoxy protons of PEG); 1.34-3.12 (20H, multiplet, protons of naloxone and PEG) ppm.

Example 2

Preparation of 6-mPEG (550 Da)-CONH-6-desoxo-naloxone (Mixture of 6-epimers)

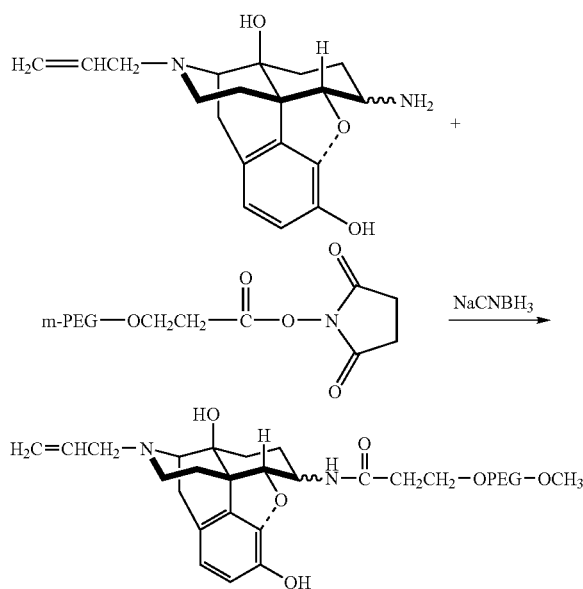

mPEG (550) N-succinimidyl propionate (Shearwater Corporation, 4.0 g, 5.5 mmol) and 6-amino-6-desoxo-naloxone (2.0 g, 6.1 mmol) (from Step A of Example 1) were dissolved in CHCl₃ (50 ml) under argon. The solution was stirred at room temperature under argon overnight (20 h). CHCl₃ (250 ml) was added and the solution was extracted with pH 1 HCl solution (3×200 ml). To the combined aqueous extracts was and extracted with CHCl₃ (3×200 ml). The CHCl₃ extracts were combined, washed with a pH 5.5 phosphate buffer solution (50 mM, 3×200 ml), dried over anhydrous Na₂SO₄ and filtered. All solvents were removed with a rotary evaporator and the resulting product was dried in vacuo for 2 days to give pure m-PEG-550-CONH-Naloxone conjugate as a colorless liquid (3.5 g, 3.7 mmol, 66% yield).

$^1$H NMR (CDCl₃): δ 7.12 and 6.88 (1H, two doublet, NHCO of α and β conjugates); 6.50-6.71 (2H, multiplet, aromatic protons of naloxone); 5.72-5.87 (1H, multiplet, olefinic proton of naloxone); 5.17 (2H, triplet, olefinic protons of naloxone); 4.58 and 4.40 (1H, two doublet, C₅ proton of α and β naloxone); 3.64 (~54H, multiplet, PEG); 3.38 (3H, singlet, methoxy protons of PEG); 0.83-3.13 (14H, multiplet, protons of naloxone) ppm.

Example 3

Synthesis of mPEG (2000 Da)-6-desoxo-naloxone

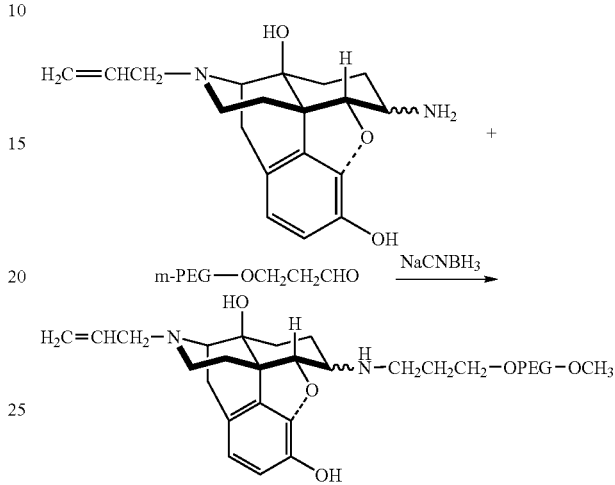

To a mixture of 6-amino-6-desoxonaloxone.2HCl (0.6 g) (from Step A of Example 1) and MPEG (2000 Da)-propionaldehyde (6.0 g) dissolved in 0.1 M phosphate buffer pH 6.5 was added phosphate buffer solution (pH 6.5, 5 ml) of NaCNBH₃. The resulting solution was stirred at room temperature under argon overnight. The reaction mixture was diluted to 500 ml, saturated with NaCl and extracted with dichloromethane. The extracted dichloromethane was dried with Na₂SO₄, evaporated and precipitated with ethyl ether. The product was dried under vacuum overnight. Yield: 5.63 g GPC: ~25% of conjugates.

The mixture product was purified through cation exchange chromatography using Poros 50 HS resin (100 ml). The mixture was dissolved in 200 ml of deionized water and was loaded on cation exchange column (3.5×28 cm). After column was washed with 500 ml of deionized water, 1N NaCl solution (500 ml) was used to elute the column. The desired conjugate was obtained after extraction with DCM, evaporation and precipitation with Et₂O. Yield: ~1.38 g.

The conjugate was further purified by reverse phase HPLC chromatography (Betasil C18 column, Keystone Scientific).

Example 4

Synthesis of MPEG (2000 Da)-6-desoxo-naloxone

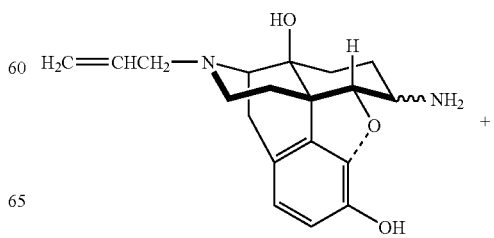

-continued

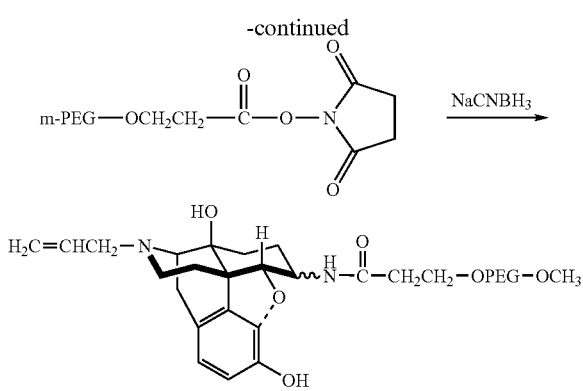

mPEG (2000 Da)-N-succinimidyl propionate (5.0 g) was dissolved in 50 ml of dichloromethane. 1.88 g of 6-aminonaloxone 2HCl (from Step A of Example 1) and 1.4 ml of triethylamine were added to the solution. The resulting solution was stirred at room temperature under argon overnight. The reaction mixture was filtered and the filtrate evaporated and precipitated with isopropanol/diethyl ether. The product was dried under vacuum overnight. It was then redissolved in 500 ml of deionized water, adjusted to pH to 9.0 with 1 N NaOH, saturated with NaCl, washed with diethyl ether, and finally extracted with dichloromethane. The extracted dichloromethane was dried with $Na_2SO_4$, the solvent removed under vacuum and the product precipitated from $Et_2O$. The product was dried under vacuum overnight.

Yield: 3.6 g. $^1H$ nmr (DMSO-$d_6$): δ 8.08 ppm and 7.53 ppm (1H, two doublets, amide H), δ 6.60-5.45 ppm (2H multi., aromatic H), δ 5.83 ppm (1H multi. olefinic H), δ 5.25-5.12 ppm (2H multi. olefinic H). δ 4.76 ppm (1H singlet). GPC: ~97% conjugation. HPLC: showed no free amino-naloxone.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A polymer conjugate according to the formula:

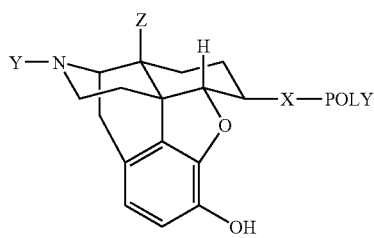

or pharmaceutically acceptable salt thereof, wherein:
Y is allyl;
Z is OH;
X is amide, amine, carbamate, sulfide, ether, thioether or urea; and
POLY is methoxy poly(ethylene glycol), wherein POLY has a molecular weight of from about 100 Da to about 2,000 Da.

2. The polymer conjugate of claim 1, wherein POLY has the formula

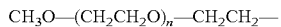

wherein n is from 2 to 45.

3. The polymer conjugate of claim 2, wherein n is from 2 to 20.

4. The polymer conjugate of claim 1, wherein POLY has a molecular weight of from about 100 Da to about 500 Da.

5. The polymer conjugate of claim 1, wherein X is amide.

6. The polymer conjugate of claim 1, wherein X is amine.

7. The polymer conjugate of claim 1, wherein X is carbamate.

8. The polymer conjugate of claim 1, wherein X is sulfide.

9. The polymer conjugate of claim 1, wherein X is ether.

10. The polymer conjugate of claim 1, wherein X is thioether.

11. The polymer conjugate of claim 1, wherein X is urea.

12. A pharmaceutical composition comprising
a polymer conjugate and
a pharmaceutically acceptable carrier
wherein the polymer conjugate has the formula:

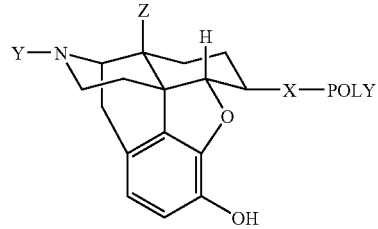

or pharmaceutically acceptable salt thereof, wherein:
Y is allyl;
Z is OH;
X is amide, amine, carbamate, sulfide, ether, thioether or urea; and
POLY is methoxy poly(ethylene glycol), wherein POLY has a molecular weight of from about 100 Da to about 2,000 Da.

13. The pharmaceutical composition of claim 12, wherein POLY has the formula

wherein n is from 2 to 45.

14. The pharmaceutical composition of claim 12, wherein n is from 2 to 20.

15. The pharmaceutical composition of claim 12, wherein POLY has a molecular weight of from about 100 Da to about 500 Da.

16. The pharmaceutical composition of claim 12, wherein X is amide.

17. The pharmaceutical composition of claim 12, wherein X is amine.

18. The pharmaceutical composition of claim 12, wherein X is carbamate.

19. The pharmaceutical composition of claim 12, wherein X is sulfide.

20. The pharmaceutical composition of claim 12, wherein X is ether.

21. The pharmaceutical composition of claim 12, wherein X is thioether.

22. The pharmaceutical composition of claim 12, wherein X is urea.

* * * * *

UNITED STATES PATENT AND TRADEMARK OFFICE
CERTIFICATE OF CORRECTION

| | | |
|---|---|---|
| PATENT NO. | : 7,662,365 B2 | Page 1 of 1 |
| APPLICATION NO. | : 11/332964 | |
| DATED | : February 16, 2010 | |
| INVENTOR(S) | : Michael David Bently et al. | |

It is certified that error appears in the above-identified patent and that said Letters Patent is hereby corrected as shown below:

In the Claims

Claim 14, line 46, "claim 12" should read --claim 13--.

Signed and Sealed this
Tenth Day of February, 2015

Michelle K. Lee
*Deputy Director of the United States Patent and Trademark Office*